United States Patent [19]

Neukermans

[11] Patent Number: 5,411,644
[45] Date of Patent: May 2, 1995

[54] METHOD OF OPERATED DUAL PUMP GETTER AND OXIDANT SENSOR AND REGULATOR

[76] Inventor: Armand P. Neukermans, 3510 Arbutus Ave., Palo Alto, Calif. 94303

[21] Appl. No.: 147,149
[22] Filed: Nov. 3, 1993
[51] Int. Cl.⁶ .................................. G01N 27/419
[52] U.S. Cl. ............................ 204/130; 204/153.18; 204/153.22; 204/421; 204/424; 204/427
[58] Field of Search .............. 204/130, 153.18, 153.22, 204/421–429

[56] References Cited

U.S. PATENT DOCUMENTS

| Re. 28,792 | 4/1976 | Ruka et al. | 204/426 |
| 3,514,377 | 5/1970 | Spacil et al. | 204/153.18 |
| 3,923,624 | 12/1975 | Beekmans et al. | 204/427 |
| 5,118,398 | 6/1992 | McElroy et al. | 204/424 |

FOREIGN PATENT DOCUMENTS 2256045 11/1992 United Kingdom .

OTHER PUBLICATIONS

Fouletier et al., "Electrically Renewable and Controllable Oxygen Getter", *Vacuum*, vol. 25, pp. 307–314, 1975 month unavailable.

Fouletier et al., "Measurement and Regulation of Oxygen Content in Gases Using Solid Electrolyte Cells III Oxygen Pump-Gauge", *J. of Appl. Electrochemistry*, vol. 5, pp. 111–120, 1975 month unavailable.

E. C. Subbarao, "Oxygen Sensors", *Ferroelectrics*, vol. 102, pp. 267–280, 1990 month unavailable.

Alcock et al., "Electrolytic Removal of Oxygen From Gases by Means of Solid Electrolyte", *J. of Appl. Electrochemistry*, vol. 2, pp. 289–299, 1972 month unavailable.

Primary Examiner—T. Tung
Attorney, Agent, or Firm—Schneck & McHugh

[57] ABSTRACT

A conduit defined by an oxygen ion permeable wall formed of zirconia or other materials and having gas permeable electrodes disposed on an inner and outer surface of the wall. The electrodes are configured to form two oxygen pumps that share an electrode on the inner surface in order to minimize interference with gas flowing through the conduit, yet allow a number of operations to be performed on the gas as it flows. The conduit can be used as a getter for removal of oxygen from even reactive gases. The conduit can also be used as a pump for injecting a known quantity of oxygen to the gas, the oxygen supplied from air outside the conduit. The upstream pump can be used as a getter and the downstream pump for oxygen injection, thereby providing a known concentration of oxygen gas or oxidants, such as water vapor, in the gas exiting the conduit. The conduit can contain a pair of sensor electrodes on the inner and outer surface downstream of the other electrodes. The sensor electrodes can determine when the oxygen removed from the gas is equal to the known quantity of oxygen injected, providing a means for measuring the concentration of oxidants in the gas.

14 Claims, 3 Drawing Sheets

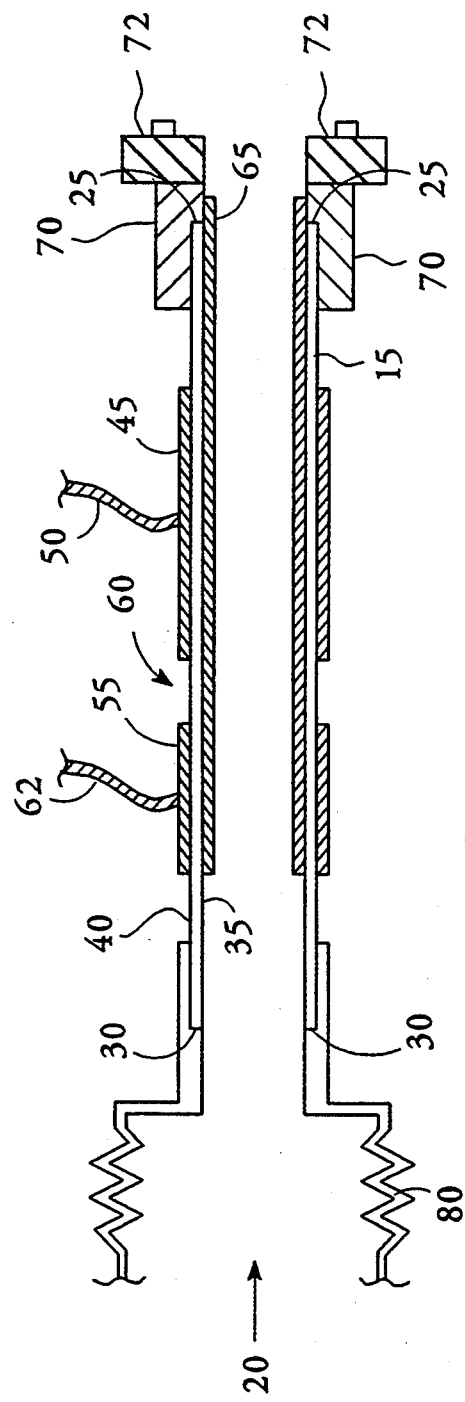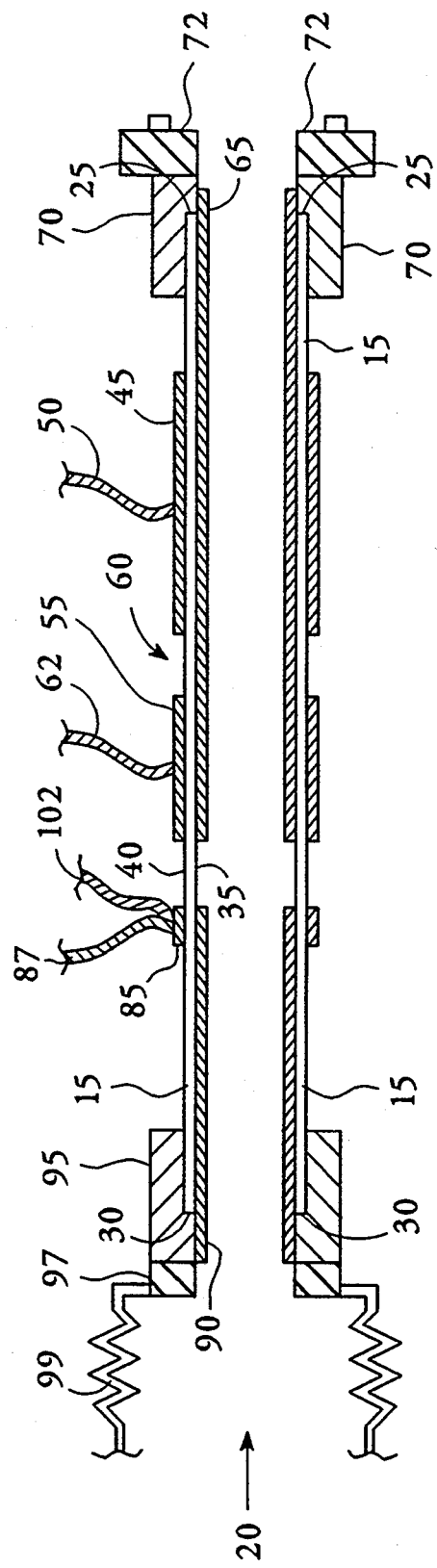

METHOD OF OPERATED DUAL PUMP GETTER AND OXIDANT SENSOR AND REGULATOR

TECHNICAL FIELD

This invention relates to a system for production or removal of oxygen atoms in gases having molecules with oxygen atoms and for measurement of oxygen and humidity levels in those gases.

BACKGROUND OF THE INVENTION

It has been established that some zirconia ($ZrO_2$) sensors, made for the measurement of oxygen concentration in gases, can also be used to remove oxygen from these gases if suitably operated. The advantages of such materials have been recognized by Fouletier et al. in an article entitled "Electrically Renewable and Controllable Oxygen Getter," *Vacuum*, vol. 25, 1975, pp. 307–314 and an article entitled "Measurement and Regulation of Oxygen Content in Gases Using Solid Electrolyte Cells III Oxygen Pump-Gauge," *J of Appl Electrochemistry*, vol. 5, 1975, pp. 111–120. Although zirconia, usually doped with yttrium ($Y_2O_3$) magnesium oxide (MgO) or lime (CaO), is the most extensively used material for these sensors, many other materials may be used, as cataloged by Subbarao in a paper entitled "Oxygen Sensors," *Ferroelectrics*, Vol. 102, 1990, pp. 267–280. Similarly doped hafnia ($HfO_2$), thoria ($ThO_2$), ceria ($CeO_2$) and bismuth trioxide ($Bi_2O_3$) are known oxygen ion conductors used for sensors. Semiconducting materials such as $TiO_2$ and $Nb_2O_3$ can also be used for sensors.

In their normal operating condition, these sensors develop a voltage which is proportional to the logarithm of the ratio of the partial pressures of oxygen on both electrodes of the device. If one electrode is in contact with a low oxygen concentration, and the other electrode is in contact with a higher pressure of oxygen, then the latter electrode will develop a positive voltage with respect to the low oxygen concentration side. This is because negatively charged oxygen ions diffuse through the zirconia away from the high pressure side, leaving a positive space charge, which in turn sets up a field which balances the diffusion. In such a mode of operation of an oxygen sensor no current flows through the device, as the flow from diffusion and the internal electric field balance each other. The developed voltage (E) is described by the Nernst equation: $E = RT \ln(p1/p2)/4F$ where R is the gas constant, T the absolute temperature, F Faraday's constant, and p1 and p2 the partial pressures of oxygen on both sides of the sensor.

If a voltage is applied of the same sign but larger than the Nernst voltage, then the device will start to draw current as oxygen ions are drawn from the low pressure electrode and flow towards the high pressure electrode. The electrodes are typically formed of platinum, which is gas permeable. Other gas permeable electrodes which may be used for sensors are known to include oxides such as $SnO_2$, $In_2O_3$ and oxides with a perovskite structure. The device works in essence as an oxygen pump, removing oxygen from the low pressure side and delivering it to the high pressure end. The oxygen which is removed may have been either free or bound to other atoms. This is termed the "extraction" mode. Oxygen atoms in the low pressure gas stream are converted at platinum molecules near the border of the low pressure electrode and the zirconia, called a "triple point" into oxygen ions, injected in the zirconia, transported through the wall, and delivered at another triple point between the high pressure platinum electrode and the zirconia where they are ejected as atoms through the electrode and into the high pressure gas stream.

Alternatively, if a voltage smaller than the Nernst voltage or of opposite sign is applied, then the current is reversed. Oxygen is now delivered from the high concentration side to the low concentration side. The pump is now working in what is termed the "injection" mode. In this case, the amount of oxygen injected can be very accurately derived from the electric current and Faraday's law. Each oxygen ion transported across the wall requires two electrons to be donated at the high pressure electrode. A gram-mole of oxygen requires $3.86 \times 10^5$ Coulombs of current, since $O_2$ gas requires four electron charges per molecule. To a very good approximation, the entire current is ionic in nature, and the electronic contribution to the current can be completely neglected.

In the case of oxygen extraction from a gas stream with an already low oxygen concentration, the current is not purely proportional to oxygen ions transported across the wall, especially for very small oxygen concentrations. In this case, especially at higher voltages, part of the ionic current may be due to zirconia decomposition, producing at first intermediate substances known as "black zirconia" and for high enough currents eventually leaving free zirconium (Zr).

Both the described pumping action due to the current and the black zirconia getter compound produced by material decomposition give rise to an extraordinary active and renewable getter material for oxygen. Somewhat less well known is the fact that these pumps can also decompose water. If the voltage is raised high enough (about 1.2 V for a typical cell at 650° C.), then it is observed that water is decomposed. The oxygen is stripped from the water, leaving hydrogen as a residual in the original gas.

Combinations of oxygen sensors and oxygen pumps have been described, for example, in an article entitled "Electrolytic Removal of Oxygen from Gases by Means of a Solid Electrolyte," *J. Appl Electrochemistry*, 2, 1972, pp. 289–299. In this article, a gas which is to be cleaned or enriched with oxygen is treated in several steps with pumps for ejection or injection of oxygen.

The same system can also be used to supply a known partial pressure of oxygen to a stream of carrier gas having a known (possibly zero) oxygen concentration. For this purpose a controlled amount of oxygen is pumped into the gas with a known current, by decreasing or reversing the voltage as described above. Given a known flow rate of carrier gas in the inner tube, the concentration of oxygen can then be determined.

In a similar way, British Patent GB 2 256 045 A to Atkinson describes a system for injection of controlled amounts of moisture in a gas stream containing some amount of hydrogen. Oxygen is pumped into a gas containing a known amount of water and hydrogen, reacting with the hydrogen, and converting it into water at the platinum electrodes. At the typical temperatures and pressures used, the equilibrium for the hydrogen-oxygen reaction is entirely pushed towards the formation of water and, to a very good approximation, every oxygen ion transported through the wall gives rise to one water molecule. Thus, given the known initial water concentration, the resultant water concentration can be accurately determined.

For a similar reason, the presence of hydrogen in a gas stream complicates the detection of oxygen atoms. When an oxygen sensor is used to determine the concentration of oxygen in a gas stream, the reading which will be obtained is dramatically affected by the presence of hydrogen. All the hydrogen in the gas stream reacts at the sensor electrode with the available oxygen, and gives rise to an oxygen reading at the electrodes which is lower than that present in the original gas stream.

While many of these phenomena are known, they are not always easy to implement. For example, various gases may need to be sealed from each other aside from oxygen ion permeable zirconia walls and platinum electrodes. Yet it may be desirable to place a number of electrodes with different functions on a sealed inner surface without interference to the gas flow from electronic leads.

An object of the present invention is to provide a device that can conveniently perform a number of useful functions utilizing the above-described phenomena.

Another object of the present invention is to provide a device for which the initial concentration of oxygen gas or oxygen containing molecules within a gas need not be known in order to produce a known concentration of such molecules.

Another object of the present invention is to provide a system for measuring in a gas an unknown concentration of molecules containing oxygen atoms.

Yet another object of the present invention is to provide a system for removing oxygen from gases that contain molecules that react with typical oxygen removal systems and interfere with such removal.

SUMMARY OF THE INVENTION

The present invention involves a uniquely configured conduit that can be used in a number of ways. The wall of the conduit, which is preferably shaped as a cylinder, is formed of yttria stabilized zirconia. A series of platinum electrodes are formed between an inlet and an outlet end of the conduit on an outside surface of the wall. Proximate to the inlet end is an extraction electrode, which is followed downstream by an injection electrode. Further downstream and adjacent to the outlet end is a sensor electrode.

A leadless platinum electrode is pasted on the inner surface of the conduit, adjacent to both the extraction and injection electrodes. This single electrode serves as an electrode for both an extraction pump and an injection pump, when used in combination with the respective extraction and injection electrodes. Downstream of this common pump electrode and also pasted on the inner surface is another sensor electrode, which is disposed adjacent to but on an opposite side of the wall from the sensor electrode on the outer surface.

The extraction electrode is separated from the injection electrode by a distance that is several times the thickness of the wall. Due to the partial electrical conductivity of the zirconia wall, this separation ensures that no cross current flows between those electrodes, the current instead flowing between each of those outer electrodes and the common electrode. Similarly, the sensor electrodes are separated from the other electrodes by a distance of several times the wall thickness, in order to electrically isolate the sensor from the pumps.

The inner sensor electrode wraps around the wall at the outlet end to provide an electrical connection outside the conduit. Similarly, the common pump electrode wraps around the inlet end of the wall to offer an electrical connection to both pumps from outside the conduit. The leadless inner electrodes offer a conduit free of protrusions that would disturb fluid flow within the conduit. In addition, this configuration of a single common electrode upstream of a sensor electrode allows efficient utilization of the inner surface of the zirconia conduit. In a preferred embodiment, these two electrodes form adjacent cylinders that coat all of the inner surface except for the small annular strip that separates them.

A vacuum tight bellows, which may be formed of stainless steel, is attached to the outlet end, the folds of the bellows providing for thermal expansion of the conduit. An vacuum tight insulator is disposed between the wrap around portions of the electrodes and the bellows to maintain the electrical integrity of the electrodes.

This configuration of two pumps and a sensor, mounted in series on a single conduit provides a number of useful functions. For example, the extraction pump alone may be operated, in which case the device acts as an efficient and renewable getter for removing oxygen atoms from the gas in the conduit. Gaseous molecules containing oxygen atoms, such as water ($H_2O$) and carbon dioxide ($CO_2$), with the exclusion of oxygen gas ($O_2$), are defined herein as "oxidants". Oxidants and oxygen gas may have their oxygen atoms removed by applying sufficient voltage to the extraction pump. For complete removal the velocity of the gas should be low enough, and the pump action sufficiently long, so that the dwell time of a plug of gas in the pump is long enough for all oxygen to diffuse to the tube walls. In this mode, the injection electrode may be open circuited, or it may be held at the same voltage as that applied to the extraction electrode, in which case it acts in combination with the extraction electrode to remove oxygen from the gas in the conduit. Such a renewable getter has applications including maintaining an oxygen free environment in certain semiconductor processing steps.

Such a getter may also be used for removing small quantities of oxygen or oxidants from reactive gases, an application beyond the capabilities of most getters. Most getters are formed of metals or plastics that will chemically react with many reactive gases. The ability of the present invention to act as a getter for reactive gases is due to the fact that the zirconia in the wall, and intermediate forms of material that may be formed in the wall as oxygen is stripped from the zirconia, such as black zirconia, are inert in the presence of most reactive gases, unlike most common getter materials. In this capacity, the electrodes on the inner surface must also be non-reactive to the gas. Platinum works well in this regard with many reactive gases, but not all. Other electrode materials that do not react with the particular gas to be flowed through the conduit may be used instead of platinum for those gases that react with platinum.

On the other hand, the injection pump alone may be operated, thereby injecting a known amount of oxygen into the conduit. The amount of injected oxygen is known from the electrical current that flows between the injection electrode and the common electrode. Each pair of electrons that flow to the injection electrode causes an oxygen ion carrying a double negative charge to flow from the injection electrode to the common electrode and be injected into the conduit.

The extraction pump may be used to supply an additional known amount of oxygen to the interior of the conduit, by causing a measured current to flow from the extraction electrode to the common electrode. It should be noted, however, that this pump cannot supply a known amount of oxygen after it has been used as an extraction pump, for the use as an extraction pump may cause the formation of intermediate forms of material such as black zirconia, which would absorb an unpredictable amount of current to be reconstituted as zirconia.

Both pumps may be operated together to provide a known concentration of molecules containing oxygen atoms within the conduit. This is accomplished by first extracting all reactive oxygen atoms from the gas flow using the extraction pump, including the reduction of oxidants such as water and removing the resulting oxygen ions. The molecules that remain after such oxidants are stripped of their oxygen atoms are defined herein as "oxidizables". If such oxidizables are present in the gas downstream near the injection pump, the oxygen ions introduced by the injection pump will first combine with those molecules.

The current that flows through the injection pump provides an accurate measurement of the number of oxygen ions injected into the conduit, which can be used to form a known concentration of oxidants. If, for example, hydrogen atoms are present in the gas flowing through the conduit, either from prior reduction of water by the extraction pump or other means, essentially all oxygen ions will combine with hydrogen to form a known concentration of water. The ability to portably and accurately provide a known concentration of water has many applications, including processing and leak simulation for semiconductor manufacturing, where a device of the present invention may be interconnected with existing gas conduits. For example, inert gases such as nitrogen ($N_2$) or argon (Ar) may be used in certain process flows, and it may be desirable to simulate a water or oxygen leak.

The sensor circuit may be employed in series with the above setup to detect if and when all hydrogen in the gas flow has been combined with oxygen from the injection pump to form water. As long as unoxidized hydrogen is present, the reaction kinetics favor immediate combination of oxygen ions transported into the conduit at the injection pump with any available hydrogen atoms. The oxygen partial pressure within the conduit at the sensor electrode is therefore very low, leading to a high voltage between the sensor electrodes. As soon as any oxygen is present that is not used to form water, the voltage in the sensor electrodes drops dramatically. The sensor can thus serve as a warning system, in this mode, for the presence of free oxygen or the depletion of all free hydrogen or other oxidizables.

If the gas flowing into the conduit is pure hydrogen, then ultrapure water of a known concentration can be supplied by injecting a known amount of oxygen at the injection pump. Ultrapure hydrogen may be created, for example, by diffusion of hydrogen gas through a heated palladium plug. The advantage of this is that small amounts of ultrapure water vapor can be made on demand, without the need for physical storage of the fluid, which usually results in contamination since ultrapure water is extremely corrosive.

The same combination of pumps can be used to accurately determine the concentration of gases such as water vapor. The extraction pump, as before, is supplied with a voltage or current designed to extract all oxygen atoms from inside the conduit. This may involve extraction of oxygen atoms from both oxygen gas molecules and gaseous water molecules, leaving hydrogen atoms inside the conduit. A measured current is then applied to the injection pump, injecting a known quantity of oxygen atoms back into the conduit. This current is increased until the voltage between the sensor electrodes drops sharply, indicating that all hydrogen atoms in the conduit have reacted to form water. This yields a determination of the hydrogen concentration created by the extraction pump, or equivalently the initial water concentration, provided that other oxygen containing compounds aside from water or oxygen were not initially present. If other such compounds are believed to be present other techniques may be employed, such as setting the voltage in the extraction pump at a level that reduces one compound but not another.

BRIEF DESCRIPTION OF THE DRAWINGS

FIG. 1 is a cross-sectional view of a dual pump conduit of the present invention.

FIG. 2 is a cross-sectional view of the conduit of FIG. 1 with a sensor incorporated downstream.

BEST MODE FOR CARRYING OUT THE INVENTION

Figure 3:
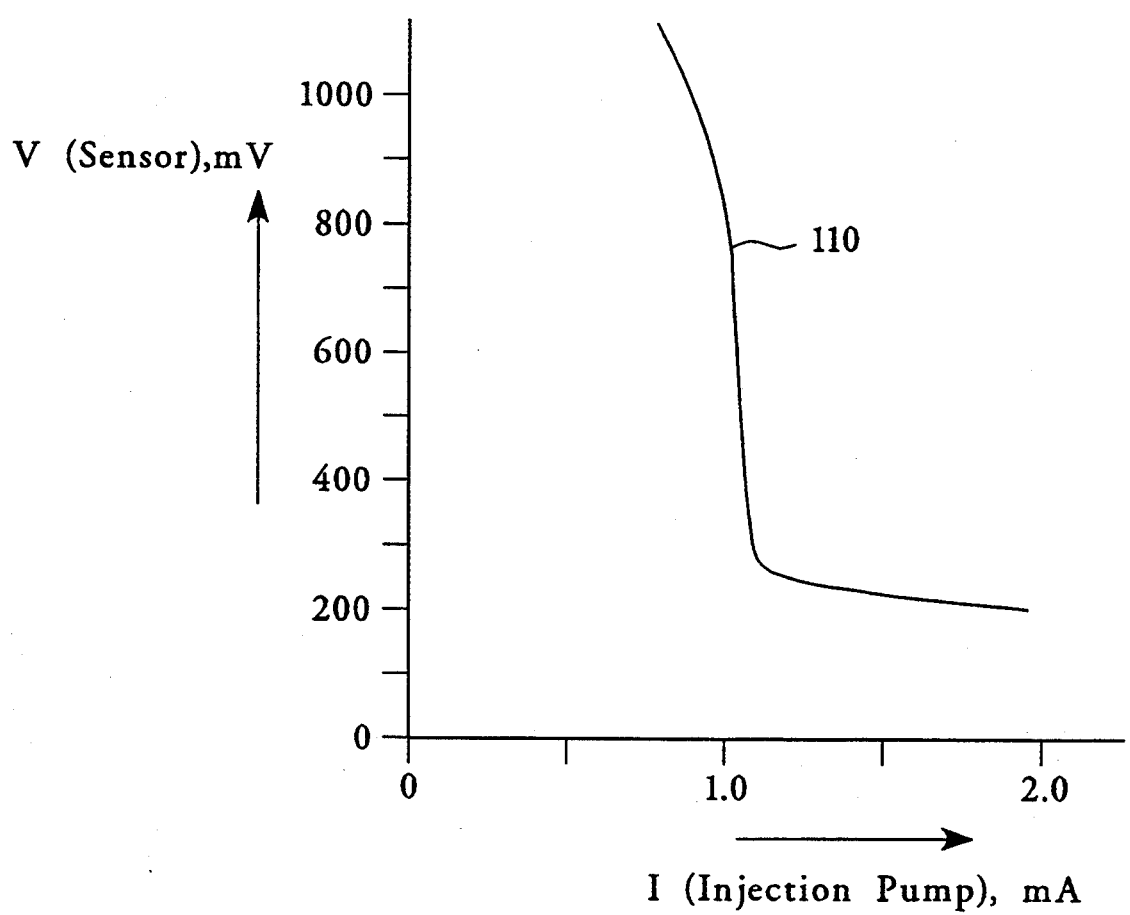
FIG. 3 is a graph of the voltage of the sensor versus the current of the injection pump.

Referring to FIG. 1, a cross-sectional view of a wall 15 comprised of zirconia ($ZrO_2$) stabilized with approximately 8% yttria ($Y_2O_3$) is shown. Other oxygen ion conducting (including semiconducting) materials known in the art may be used for the well 15 instead, depending upon the particular application desired. In the preferred embodiment shown, the wall 15 is formed into a cylinder that defines a conduit 20. The cylindrical conduit 20 may have a diameter of from one quarter to one half inch for most applications, although larger and smaller diameters are also envisioned. The conduit 20 has an inlet end 25 and an outlet end 30, which may be separated by a length of six to eighteen inches for conduits having diameters in the range of one quarter to one half inch. The wall 15 has an inner surface 35 and an outer surface 40, and is of a generally uniform thickness which may be up to one tenth of an inch.

An extraction electrode 45 formed of platinum (Pt) paste has been painted on the outside surface 40 near the inlet end 25. The extraction electrode 45 is generally cylindrical in shape and is connected near its center to a lead 50, to enable the application of electrical voltage and current to the electrode 45. Downstream of the extraction electrode 45 is an injection electrode 55 which is also comprised of platinum and painted on the outer surface 40. The injection electrode 55 is separated from the extraction electrode 45 by a space 60 that is several times as long as the wall 15 is thick. Another electrical lead 62 is connected to the injection electrode 55 near its center.

Most of the inner surface 35 of the wall 15 has also been painted with a platinum electrode, denoted a common electrode 65. The common electrode 65 is generally cylindrical and extends from the inlet end 25 which it may wrap around or, as shown, protrude from the inlet end 25 of the wall 15 in order to offer electrical connection with a terminal 70 for providing electrical voltage or current to the common electrode 65. The terminal 70 is molded to a VCR flange 72 for vacuum tight coupling to other elements, not shown. The common terminal extends downstream toward the outlet end 30, but terminates prior to reaching the outlet end 30 of the wall 15. Preferably, the common electrode 65 coats the entire inner surface 35 of the conduit between the inlet end 25 and its termination near the outlet end 30. The extraction electrode 45 is separated from the terminal 70 by a distance that is several times the wall 15 thickness.

It should be noted that materials other than zirconia may be used for the wall 15 provided that the wall 15 conducts oxygen ions in response to differing oxygen gas pressures and electrical voltages on the inner and outer surfaces, 35 and 40. Examples of such materials are doped $HfO_2$, $ThO_2$, $CeO_2$, $Bi_2O_3$, $TiO_2$ and $Nb_2O_3$. As with the electrodes, for certain applications it is desirable that the wall 15 not react with caustic gases. For these applications, the wall 15 may be formed primarily of zirconia or hafnia.

It should also be noted that the electrodes 45, 55 and 65 could be formed of other materials, although platinum is preferred. Any electrically conductive, gas permeable material could be used, examples of which are gold and silver. Other members of the platinum group besides platinum, such as iridium (Ir), rhodium (Rh) and rutinium (Ru) may also be used, as well as alloys combining these elements. Oxides and perovskites known in the art may alternatively be used. For certain applications described below, it is also preferable that the electrodes are composed of substances that, like platinum, do not react with many reactive gases. For these applications, alloys such as $Pt_{0.92}Ir_{0.08}$ may be desirable. Knowledge of the reactive gas to be flowed through the conduit 20 can be used to select electrodes that do not react with that gas.

Affixed to the outlet end 30 of the wall 15 is a gas tight bellows 80, which may be formed of stainless steel, or other strong, flexible materials impervious to heat and caustic gases. The bellows 80 is also generally cylindrical in shape, and has folds in its length to absorb stress created by thermal expansion and contraction of the conduit 20 in response to temperature changes.

To use this device as a getter, a stream of gas may be flowed through the conduit from the inlet end 25 to the outlet end 30. Preferably the stream of gas already has a low concentration of oxygen containing gas molecules, or oxidants. A "low" concentration is hereby defined as 200 parts per million (ppm) or less, whereas a "high" concentration is defined as above 200 ppm. The zirconia wall 15 is, as described above, permeable to oxygen ions, allowing such ions to flow through the wall 15 from a gas having a higher oxygen gas partial pressure to one with a lower partial pressure. The ions carry with them a negative charge that tends to repel the flow of further ions across the wall 15, quickly reaching an equilibrium voltage (E) at which ion flow through the wall 15 has stopped according to the Nernst equation, $E=RT\ln(p1/p2)/4F$.

Thus, for the situation in which the gas inside the conduit has an oxygen partial pressure below that of the gas outside the conduit, the outside surface 45 of the wall 15 naturally develops a positive voltage compared to the inner surface 35, the positive voltage acting to stop migration of oxygen ions from outside the conduit 20 to inside the conduit 20. If a voltage is applied via the gas permeable electrodes 45 and 65 to the outside surface 40 relative to the inside surface 35 that is above this equilibrium voltage, oxygen ions will be caused to flow from the lower oxygen pressure environment within the conduit 20 to the higher oxygen pressure environment without the conduit 20, in effect operating as an extraction pump for oxygen.

If the voltage of the extraction electrode 45 is high enough above that of the common electrode 65, oxidants within the conduit 20 will be stripped of their oxygen atoms, which will be transported as ions through the wall 15 to outside the conduit 20. A typical temperature of operation which is convenient for the operation of such a zirconia, pump is 450–1000 degrees Celsius, and as such an oven, not shown, may be useful. At an operating temperature of 650° C., a voltage of 12 V or above is sufficient to decompose water and remove oxygen. For certain materials, such as carbon dioxide ($CO_2$), it may be desirable to remove only an active or easily removed oxygen atom from each $CO_2$ molecule, thereby yielding carbon monoxide (CO).

For conditions including low oxygen partial pressures within the conduit 20 and high voltages across the wall 15 for extracting oxygen from within the conduit 20, the zirconia in the wall may be stripped of some oxygen atoms, resulting in substances intermediate between zirconia ($ZrO_2$) and zirconium (Zr) termed black zirconia, and eventually resulting in zirconium. Black zirconia is electrically reversible into zirconia simply by lowering the voltage below the equilibrium voltage and causing oxygen ions to flow into it. It is also reversible into zirconia by contact with a sufficient amount of oxygen gas. As such, black zirconia is an efficient oxygen getter, and may have oxygen vacancies in its crystal lattice that attract oxygen. Zirconium, however, is not electrically reversible into black zirconia or zirconia, and thus some care must be taken not to break down the wall 15 into zirconium. Holding the current density at the common electrode 65 below 200 milliamperes (mA) per square centimeter (cm) should avoid such irreversible breakdown.

The reversibility of black zirconia in the presence of oxygen offers a substantial practical advantage. With many common getters, accidental exposure to air destroys the device. With the present invention, however, accidental exposure to air is not a problem, since black zirconia can be re-created by application of sufficient voltage or current between the extraction electrode 45 and common electrode 65 at low oxygen pressures within the conduit 20.

In many cases it is of interest to remove small amounts of oxygen or oxidants not only from inert gases but also from such reactive gases as anhydrous hydrofluoric or hydrochloric acid, chlorine, or many other reactive vapors. This may be of particular advantage in certain semiconductor manufacturing processes. Most existing metal getters are not suitable for this purpose, since they react very strongly with these compounds at the temperature of operation. The extraction pump described above, however, would only need to expose platinum, zirconia and black zirconia to such reactive gases.

Since black zirconia derives its oxygen scrubbing properties from oxygen vacancies in its crystal lattice rather than from chemical affinities, it is mostly inert in the presence of reactive gases, behaving very much like ordinary zirconia in this respect. Zirconia and platinum are extremely inert substances, although platinum can act as a catalyst for some reactions. For this reason, it may be advantageous to lower the temperature of operation to 350°–500° C. and preferably to 400°–450° C. for use with some gases. This lowers the catalytic action of the platinum and the possibility of degradation of the electrode, while only slightly slowing the pumping action of the wall 15. When using corrosive gases at such temperatures, it may be advisable to surround the conduit 20 with another tube which is shatter proof.

The inertness of zirconia and the derived black zirconia getter in the presence of such reactive gases has been confirmed in tests. For example, in tests of propane at 650° C., all components were found to be inert. In tests of HCl at 650° C., the zirconia compounds were found to be inert, but the platinum electrodes showed some reactivity.

Alternatively hafnia, which is chemically very similar to zirconia, or a combination of hafnia and zirconia, could form the wall 15 for use with reactive gases. A reactive gas is defined in this application as any gas which is not inert. Alloys based on combinations of platinum group elements, such as platinum alloyed with 8–12% iridium, may provide improved chemical resistance to reactive gases. An additional method that can be used for reactive gases is to select electrode materials, at least for those electrodes disposed on the inner surface 35, based upon the gas that is to be flowed through the conduit. In this manner, materials that do not react with the gas to be flowed can be selected for those electrodes.

For many applications, removal of all oxygen gas or oxidants as described above may be the primary desired use of the conduit. For many other applications, it may be desired to have an exact, known concentration of oxygen atoms or oxidants in the gas. This can be provided by applying an electrical current to the injection electrode 55, in concert with the above described voltage applied between the extraction electrode 45 and the common electrode 65. Oxygen atoms disposed near the junction between the injection electrode 55 and the wall 15 acquire a pair of electrons from the electrode 55 and are then transported as oxygen ions across the wall 15 to the common electrode 65, where they give up their pair of electrons to that electrode 65 to emerge as oxygen atoms within the conduit. The electrical current between the injection electrode 55 and the common electrode 65 provides an accurate measurement of the number of oxygen atoms transported from outside to inside the conduit 20.

In other words, once all the oxygen or oxidants have been removed from the gas by the voltage applied between the common electrode 65 and the extraction electrode 45, the transport of a known quantity of oxygen ions from the outer surface 40 to the inner surface 35 via a current supplied from the injection electrode 55 to the common electrode 65 injects a known quantity of oxygen into the conduit 20 downstream of the extraction electrode 45.

For the situation in which oxygen had been extracted from oxidants at the extraction pump, leaving oxidizable molecules in the gas inside the conduit 20, then oxygen atoms injected into the conduit 20 downstream at the injection pump will first combine with those oxidizables to form oxidants, essentially to the exclusion of oxygen gas. Thus the concentration of those oxidants produced in the gas can be determined by the amount of oxygen introduced at the injection pump and the chemical formula of the oxidant. For example, if the oxidant created is water vapor ($H_2O$), each oxygen atom introduced goes toward the creation of one water molecule, at least to the point where essentially all available hydrogen atoms have been used, beyond which point further oxygen atoms introduced may form oxygen gas ($O_2$). As long as the flow rate of the gas through the conduit 20 is known, the concentration of oxidants can be accurately predicted.

It should be mentioned that this accurate measurement of oxidant content within the conduit could not be achieved with a single pump used for both extraction and injection of oxygen, since the formation of black zirconia during the extraction phase would absorb an imprecise amount of current during the injection phase.

Referring now to FIG. 2, the apparatus shown in FIG. 1 has been expanded by the addition of a pair of sensor electrodes downstream of the common electrode 65 and the injection electrode 55. An outer sensor electrode 85 is separated from the injection electrode 55 and the common electrode 65 by a distance of several times the wall 15 thickness, ensuring the electrical independence of the electrodes from each other due to the limited conductivity of the wall 15. The outer sensor electrode 85 can be very narrow, which is favorable for accurate temperature calibration. A platinum lead 87 is connected to the electrode 85. An inner sensor electrode 90 is similarly separated from the common electrode 65 and the injection electrode 55 by a distance of several times the thickness of the wall 15, and the two sensor electrodes are positioned adjacent to each other on opposite surfaces of the wall 15. The outer sensor electrode 85 terminates before reaching the outlet end 30 of the wall 15, and is separated from an electrically conductive sensor terminal 95 by a distance of substantially greater than the wall 15 thickness. The sensor terminal 95 is connected to the inner sensor electrode 90, which either extends beyond the outlet end 30 of the wall 15 as shown, or wraps around that end of the wall 15, which is not shown. The sensor electrodes, like the other electrodes, are preferably formed of platinum paste which has been painted on the wall 15.

A gas tight insulator 97, which may be formed of glass, ceramic or alumina, is affixed at the outlet end 30 to electrically separate the sensor electrode 90 and terminal 95 from a gas tight, flexible, stainless steel bellows 99. As before, the bellows has folds that allow for thermal expansion and contraction of the length of the conduit 20.

The sensor electrodes 85 and 90 provide a means for determining the concentration of oxygen gas within the conduit 20. If the oxygen gas partial pressure outside the conduit is known, as well as the temperature, then it is possible to determine the oxygen gas partial pressure within the conduit using the Nernst equation. In this case the sensor requires a temperature calibration, which may be provided using a lead 102 formed of a platinum-rhodium (PtRh) alloy wire which is joined to lead 87 to form a thermocouple device, as is known in the art.

Referring now to FIG. 3, the sensor may also be used to check the concentration of the gas downstream of the injection pump for the presence of free oxygen. Curve 110 is a plot of sensor voltage verses injection pump current for typical operating conditions. In the absence of oxygen gas within the conduit 20, the voltage between the sensor electrodes will be high, on the order of 1000 mV. This lack of oxygen may be due to the presence of oxidizables that have been created at the extraction pump. The presence of such oxidizables downstream at the injection pump leads to absorption of essentially all oxygen atoms introduced by that pump before the gas within the conduit has traveled further downstream to the sensor. When all available oxidizables have reacted with oxygen introduced into the conduit 20 at the injection pump, however, free oxygen may be present at the sensor, leading to a dramatic reduction in voltage between the sensor electrodes.

FIG. 3 displays the voltage across the sensor electrodes 85 and 90 as the electrical current between the injection electrode 55 and the common electrode 65 is changed for a typical concentration of oxidizables within the conduit. For currents below about 1 milliampere the sensor voltage is high, typically 700 to 1200 millivolts, indicating oxygen concentrations on the order of $10^{-16}$ or less within the conduit 20. At about that current, however, the sensor voltage drops precipitously with a small increase in current, which is due to the depletion of all available oxidizables in the conduit and the creation of free oxygen. AS the injection pump current continues to increase, the decrease in the voltage across the sensor becomes much more gradual, indicating that the conduit is no longer switching from a state of virtually no free oxygen to some free oxygen, but is instead increasing in oxygen content in a linear relationship to the injector pump current.

The sensor voltage can therefore serve as a warning for the presence of free oxygen for those applications in which free oxygen is deleterious. For example, it may be desired to create water vapor that lacks oxygen gas. If the sensor voltage drops suddenly, it is an indication that all oxidizable hydrogen present in the conduit has been depleted to produce water and oxygen gas is present at the outlet. Thus, the sensor can be monitored to ensure that the conduit is operating in a safe zone during the production of oxidants.

When both the extraction and injection pumps are operated, an inflection of the sensor voltage occurs at the point where the amount of oxygen introduced at the injection pump matches the amount of oxidants in the conduit downstream of the extraction pump. The conduit 20 can therefore be used to measure the concentration of an oxidant in a gas. For example, with a gas flowed at a measured rate through the conduit 20, the extraction pump can be employed to remove all oxidants from the conduit 20. The current in the injection pump can then be gradually increased, while the voltage of the sensor is closely watched. When the voltage in the sensor drops precipitously, indicating a precise match between the number of oxygen atoms introduced at the injection pump and the number of oxygen atoms needed for oxidation of the oxidizables created by the extraction pump, the current in the injection pump provides a means for determining the concentration of oxidants in the original gas.

Since each oxygen ion transported at the injection pump requires two electrons from the injection electrode 55, and oxygen gas ($O_2$) requires four electron charges per molecule, a gram-mole of oxygen gas requires $3.86 \times 10^5$ coulombs of current. Where, for example, the concentration of hydrogen in a gas such as nitrogen is desired to be measured, the reaction for water requires the addition of two moles of hydrogen for each mole of oxygen. Thus the hydrogen concentration in the gas is twice the amount of oxygen introduced at the injection pump that causes the sensor voltage to drop precipitously, divided by the flow rate of the gas. If instead, the concentration of water vapor in a gas is sought to be measured, each mole of oxygen flowed into the conduit at the injection pump corresponds to a mole of water reduced at the extraction pump. In this case, the flow of oxygen added at the injection pump at the inflection of the sensor, divided by the flow rate of the gas within the conduit, provides the concentration of water in the gas.

Figure 4:
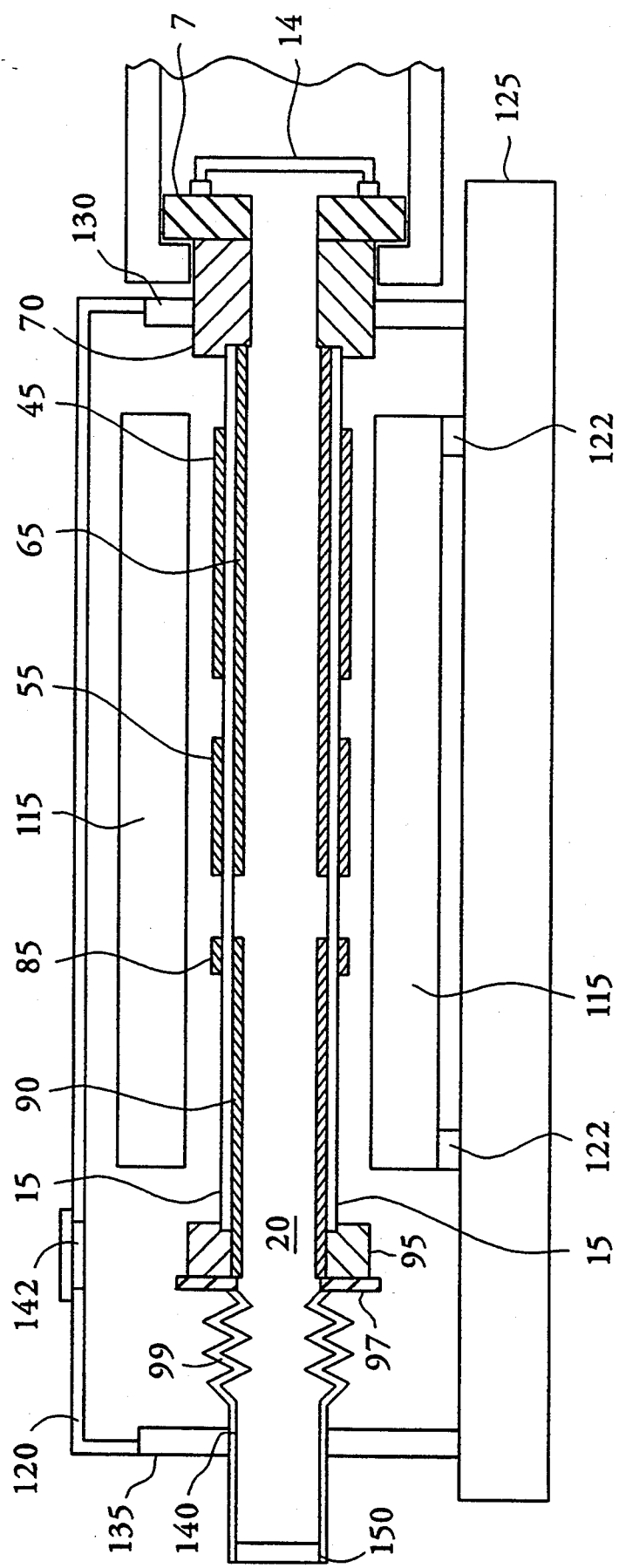
FIG. 4 is a cross-sectional view of the conduit of FIG. 2 housed within an oven.

Referring now to FIG. 4, the conduit 20 of FIG. 2 is shown disposed within an oven 115. The oven 115 heats the wall 15, and electrodes 45, 55, 65, 85 and 90 to temperatures favorable for operation of the conduit, which may be 450°–1000° C. for use with inert gases and slightly lower for use as a getter of reactive gases. The oven may be generally cylindrical to surround the outside of the conduit 20. A cylindrical cover and seal 120 surrounds the oven 115. The oven is supported from below by stands 122 on a platform 125, which also supports a side wall 130 at the inlet end and another side wall 135 at the outlet end. The terminals 70 protrude through the sidewall 130 at the inlet and hold the conduit affixed thereto. A straight section 140 of the bellows 99 protrudes through the sidewall 135 at the outlet, providing vertical support yet lateral freedom for thermal expansion or contraction of the wall 15.

For clean operation, the air within the cover 120 is maintained free of particles. Provisions such as a filter covered opening 142 in the cover 120, should be included to allow air to be supplied to outside the conduit 20. A ferrule filter 145 is incorporated into the VCR flange 72 and is disposed across the inlet to the conduit 20. Another ferrule filter 150 is disposed across the bellows 99 at the outlet. The filters 145 and 150 provide for removal of particles from the gas flowing into and out of the conduit 20.

I claim:

1. A method of providing a known amount of oxygen atoms to a gas comprising:
providing an oxygen ion conductive electrolyte wall having an outer surface in contact with air and an inner surface defining a conduit,
flowing a gas through said conduit,
extracting substantially all active oxygen atoms from oxidants in said gas by transporting oxygen ions through said wall and into said air near an inlet end of said conduit, and
injecting a known quantity of oxygen atoms from said air into said gas by transporting oxygen ions through said wall downstream of said extraction of substantially all oxygen atoms.

2. The method of claim 1 wherein extracting said oxygen atoms from oxidants in said gas includes applying a voltage to said outer surface of said wall relative to said inner surface of said wall that exceeds an equilibrium voltage extant between said surfaces due to different oxygen gas pressures inside and outside said conduit, such that oxygen ions are transported from said inner surface to said outer surface.

3. The method of claim 2 wherein said gas is reactive to plastic getters.

4. The method of claim 1 wherein injecting a known quantity of oxygen atoms to said gas includes causing a known electrical current to flow from said outer surface of said wall to said inner surface of said wall, thereby transporting a known quantity of oxygen ions through said wall to inside said conduit.

5. The method of claim 1 wherein said gas is reactive to metal getters.

6. The method of claim 1 further comprising providing a sensor on said conduit downstream of said injection of oxygen atoms and monitoring for the presence of free oxygen in said gas with said sensor, including watching for a sudden change in a voltage of said sensor as said known quantity of oxygen atoms injected is gradually changed.

7. The method of claim 1 wherein said wall is made of a material including at least one compound from the group consisting of $ZrO_2$, $HfO_2$, $ThO_2$, $CeO_2$, $Bi_2O_3$, $TiO_2$ and $Nb_2O_5$.

8. The method of claim 1 wherein said oxidants include $H_2O$.

9. A method for determining a concentration of an oxidant in a gas comprising:
   providing an oxygen ion permeable electrolyte wall having an outer surface at least partly in gaseous communication with air and an inner surface defining a conduit, said conduit having an inlet end and an outlet end and having an extraction pump disposed on said wall near said inlet end, a sensor disposed on said wall near said outlet end and an injection pump disposed on said wall between said extraction pump and said sensor,
   flowing a gas at a measured rate through said conduit from said inlet end to said outlet end,
   extracting substantially all oxygen atoms from oxidants in said gas by transporting oxygen ions through said wall to said air via said extraction pump, thereby leaving oxidizables within said conduit instead of said oxidants,
   injecting a known quantity of oxygen atoms to said gas downstream of said extraction of oxygen atoms, by transporting oxygen ions taken from said air through said wall via said injection pump,
   monitoring said sensor to watch for the presence of free oxygen in said gas, thereby indicating that all oxidants have been oxidized with said known quantity of oxygen atoms, and
   calculating said concentration of said oxidants from said known quantity of oxygen atoms.

10. The method of claim 9 wherein said gas is reactive to metal getters.

11. The method of claim 10 wherein said gas is reactive to plastic getters.

12. The method of claim 9 wherein said oxidants include $H_2O$.

13. The method of claim 9 wherein said oxidants include $CO_2$.

14. The method of claim 9 wherein said monitoring includes watching for a sudden change in a voltage of said sensor as said known quantity of oxygen atoms injected is gradually increased.

* * * * *

UNITED STATES PATENT AND TRADEMARK OFFICE
CERTIFICATE OF CORRECTION

PATENT NO. : 5,411,644
DATED      : May 2, 1995
INVENTOR(S) : Armand P. Neukermans It is certified that error appears in the above-indentified patent and that said Letters Patent is hereby corrected as shown below:

Title page, item [54] and column 1, line 2:   "OPERATED" should read - - OPERATING - -.

Column 1, line 1, in the title, "OPERATED" should read - - OPERATING - -.

Column 8, line 16, "zirconia, pump" should read - - zirconia pump - -.

Column 8, line 18, "voltage of 12" should read - - voltage of 1.2 - -.

Column 11, line 23, "AS" should read - - As - -.

Signed and Sealed this

Twenty-eighth Day of November 1995

Attest:

BRUCE LEHMAN

*Attesting Officer*   *Commissioner of Patents and Trademarks*